United States Patent
Hutchings et al.

(10) Patent No.: US 10,426,397 B2
(45) Date of Patent: Oct. 1, 2019

(54) INFORMATIVE SYSTEM USING AND INSTRUMENTED AND CONNECTED HAIRBRUSH

(71) Applicant: WITHINGS, Issy les Moulineaux (FR)

(72) Inventors: Cedric Hutchings, Issy les Moulineaux (FR); Eric Carreel, Meudon (FR)

(73) Assignee: WITHINGS, Issy les Moulineaux (FR)

( * ) Notice: Subject to any disclaimer, the term of this patent is extended or adjusted under 35 U.S.C. 154(b) by 230 days.

(21) Appl. No.: 14/760,801

(22) PCT Filed: Jan. 13, 2014

(86) PCT No.: PCT/FR2014/050051
§ 371 (c)(1),
(2) Date: Jul. 14, 2015

(87) PCT Pub. No.: WO2014/111646
PCT Pub. Date: Jul. 24, 2014

(65) Prior Publication Data
US 2015/0342515 A1     Dec. 3, 2015

(30) Foreign Application Priority Data
Jan. 15, 2013   (FR) ...................... 13 50345

(51) Int. Cl.
*A46B 15/00* (2006.01)
*A61B 5/00* (2006.01)
(Continued)

(52) U.S. Cl.
CPC .............. *A61B 5/448* (2013.01); *A46B 9/023* (2013.01); *A46B 15/0006* (2013.01);
(Continued)

(58) Field of Classification Search
CPC .......... A45D 1/18; A45D 2/002; A45D 24/00; A45D 24/10; A45D 2044/007;
(Continued)

(56) References Cited

U.S. PATENT DOCUMENTS 3,850,181 A * 11/1974 Baker ................. A45D 24/007
                                                        132/119.1
3,946,606 A *  3/1976 Abrioux ................ G01L 1/044
                                                        132/219
(Continued)

FOREIGN PATENT DOCUMENTS

| CA | 1323411 C * | 10/1993 | ............. H05K 17/97 |
| EP | 1297781 A1 | 2/2003 | |
| FR | 2964023 A1 | 2/2012 | |

OTHER PUBLICATIONS

International Search Report Application No. PCT/FR2014/050051 report dated Apr. 24, 2014.

*Primary Examiner* — Tatiana L Nobrega
(74) *Attorney, Agent, or Firm* — Miller, Matthias & Hull LLP

(57) ABSTRACT

Hairstyling tool of the comb or hairbrush type, comprising a handle and a body, an electric battery a force sensor, an electronic unit configured to capture and format signals provided by the sensors, a wireless communication means for transmitting data to a remote entity, by means of which information about the movements executed by the tool and the forces it undergoes can be transmitted to the remote entity, the remote entity being able to send information back to the user of the tool about the hair being styled.

6 Claims, 2 Drawing Sheets

(51) Int. Cl.
*A46B 9/02* (2006.01)
*H04B 7/26* (2006.01)
*A45D 24/02* (2006.01)
*A45D 24/00* (2006.01)

(52) U.S. Cl.
CPC .......... *A46B 15/0038* (2013.01); *A45D 24/00* (2013.01); *A45D 24/02* (2013.01); *A45D 2024/002* (2013.01); *H04B 7/26* (2013.01)

(58) Field of Classification Search
CPC ............ A46B 15/0006; A46B 15/0002; A46B 15/0012; A46B 15/0038; A61B 5/448
USPC .................................. 132/212, 219; 607/79
See application file for complete search history.

(56) References Cited

U.S. PATENT DOCUMENTS

| | | | | |
|---|---|---|---|---|
| 4,167,869 A * | 9/1979 | Gikas | ..................... | A45D 24/10 132/219 |
| 4,857,702 A * | 8/1989 | Cafaro | ..................... | A45D 1/04 219/225 |
| 5,307,825 A * | 5/1994 | Smith | ..................... | A45D 24/00 132/112 |
| 7,472,577 B2 * | 1/2009 | Shibuichi | ................. | A61B 7/00 73/9 |
| 8,151,624 B2 * | 4/2012 | Sherman | ................ | G01N 19/02 73/9 |
| 2003/0233861 A1 * | 12/2003 | Woolston | ............... | G01N 19/02 73/9 |
| 2008/0102953 A1 | 5/2008 | Schultz | | |
| 2008/0219528 A1 * | 9/2008 | Edgar | ................. | A45D 44/005 382/128 |
| 2009/0064430 A1 * | 3/2009 | Jimenez | ............. | A46B 15/0002 15/22.1 |
| 2009/0071228 A1 * | 3/2009 | Sherman | ................ | G01N 19/02 73/9 |
| 2009/0106998 A1 * | 4/2009 | Brown-Carter | ........ | A45D 20/10 34/90 |
| 2009/0147081 A1 * | 6/2009 | Hanson | .................. | A45D 20/12 348/77 |
| 2011/0247156 A1 * | 10/2011 | Schmid | .............. | A46B 15/0002 15/105 |
| 2011/0275424 A1 * | 11/2011 | Schmid | .............. | A46B 15/0002 463/1 |
| 2011/0314677 A1 * | 12/2011 | Meier | ..................... | A46B 5/0062 30/41.8 |
| 2012/0312320 A1 * | 12/2012 | Humphreys | ............. | A45D 1/04 132/211 |
| 2013/0255380 A1 * | 10/2013 | Salsman | ................ | G01P 15/093 73/514.26 |
| 2015/0164407 A1 * | 6/2015 | Hyde | ................ | A46B 15/0055 600/301 |

* cited by examiner

INFORMATIVE SYSTEM USING AND INSTRUMENTED AND CONNECTED HAIRBRUSH

CROSS-REFERENCE TO RELATED APPLICATIONS

This application is a 35 USC § 371 U.S. national stage filing of International Patent Application No. PCT/FR2014/050051 filed on Jan. 13, 2014, which claims priority under the Paris Convention and 35 USC § 119 to French Patent Application No. 13 50345, filed on Jan. 15, 2013.

FIELD OF THE DISCLOSURE

The present invention relates to hairstyling tools such as a comb or hairbrush, and systems incorporating such hairstyling tools.

BACKGROUND OF THE DISCLOSURE

More particularly, the invention relates to a hairstyling tool having a body and a handle, used by a user to style or more generally to maintain his or her hair.

When the tool travels along a section of hair, it is subjected to the forces generated by the resistance of the hair engaged in the bristles or teeth of the body of the tool. These forces are variable and in a sense are representative of the health or deficiencies of the hair. However, it is very difficult for a user to interpret these forces or the variations in these forces.

There is therefore a need for a solution providing a better interpretation of the forces and motions involved in the styling actions performed by a user.

SUMMARY OF THE DISCLOSURE

To this end, the invention proposes a hairstyling tool of the comb or brush type, comprising:
  a handle and a body provided with teeth and/or bristles,
  a battery for storing electricity,
  at least one movement sensor or accelerometer,
  an electronic control unit, configured to capture and format signals provided by said sensor,
  at least one wireless communication means suitable for data transmission to a remote entity,
whereby information on the movements executed by the tool can be transmitted to the remote entity.

In addition, said hairstyling tool is integrated into a system comprising at least one remote entity which can be connected to the tool by a wireless connection.

With these arrangements, the data captured by the sensor can be processed by the one (or multiple) remote entity(s), which in return can provide the user of such a brush with information about the hair being styled.

In addition, the user can be informed of certain data captured by the sensor, on a display screen of a mobile device for example such as a smartphone or in a web browser in another example.

In some embodiments of the invention, one or more of the following arrangements may possibly be used:

the hairstyling tool may further comprise at least one force sensor suitable for measuring a torsional or bending stress exerted between the handle held by a user and the body engaged with the hair of said user, the electronic unit being configured to format and transmit these additional data; whereby information about the stresses generated by the hairstyling movement can be transmitted in addition to the movement to the remote entity in order to obtain a more complete analysis;

the hairstyling tool may further comprise at least one camera and/or optical sensor suitable for capturing images (particularly of the hair or scalp), the electronic unit being configured to format and transmit these images; whereby the images can be transmitted as additional data to the remote entity in order to obtain an even more complete analysis;

the hairstyling tool may further comprise at least one microphone suitable for measuring the friction generated by the hairstyling movement, the electronic unit being configured to format and transmit the corresponding data; whereby vibration analysis can be used to refine the data analysis concerning the hair;

the hairstyling tool may further comprise at least one temperature sensor and/or humidity sensor, to capture the current characteristics of the atmospheric environment; whereby the environmental conditions are used to refine the data analysis concerning the hair;

the hairstyling tool may further comprise at least one memory space suitable for storing data collected during the hairstyling movement or movements, prior to subsequent transmission to the remote entity; so that use of the wireless link can be minimized, and in addition so that the data are not lost in case of temporary unavailability of the wireless connection.

The invention also provides an informational system comprising a hairstyling tool as described above, and a remote entity formed of a smartphone type of mobile device which can be connected to said hairstyling tool by a wireless connection and configured to display data transmitted by the hairstyling tool.

In addition, the remote entity may be formed of a mobile device, for example a smartphone, configured to display some of the data transmitted by the hairstyling tool and provide information to the user about the hair being styled.

In addition, the remote entity may comprise both a mobile device and a computer server that can connect to the mobile device in order to exchange summary data concerning the styling.

The invention also provides a method implemented in an informational system as described above, the method comprising the steps of:
  a—capturing information relating to at least the hairstyling movements of a user,
  b—transmitting the data corresponding to such information to a remote entity formed of a smartphone type of mobile device,
  c—displaying said corresponding data on a screen of the remote entity,
  f—providing feedback about the hair being styled, to the user of the tool.

In addition, the remote entity may be formed of a mobile device, and the information about the hair being styled is provided to the user by an electronic message on the mobile device.

In addition, the method may possibly include the steps of:
  d—transmitting summary data concerning the hairstyling to the server,
  e—receiving back from the server recommendations for hair care or products to be applied to the hair concerned and displaying them on the mobile device.

Other features and advantages of the invention will be apparent from the following description of one of its embodiments, given by way of non-limiting example with reference to the accompanying drawings.

BRIEF DESCRIPTION OF THE DRAWINGS

In the drawings.

In the various figures, the same references designate identical or similar elements.

DETAILED DESCRIPTION OF THE DISCLOSURE

Figure 1:
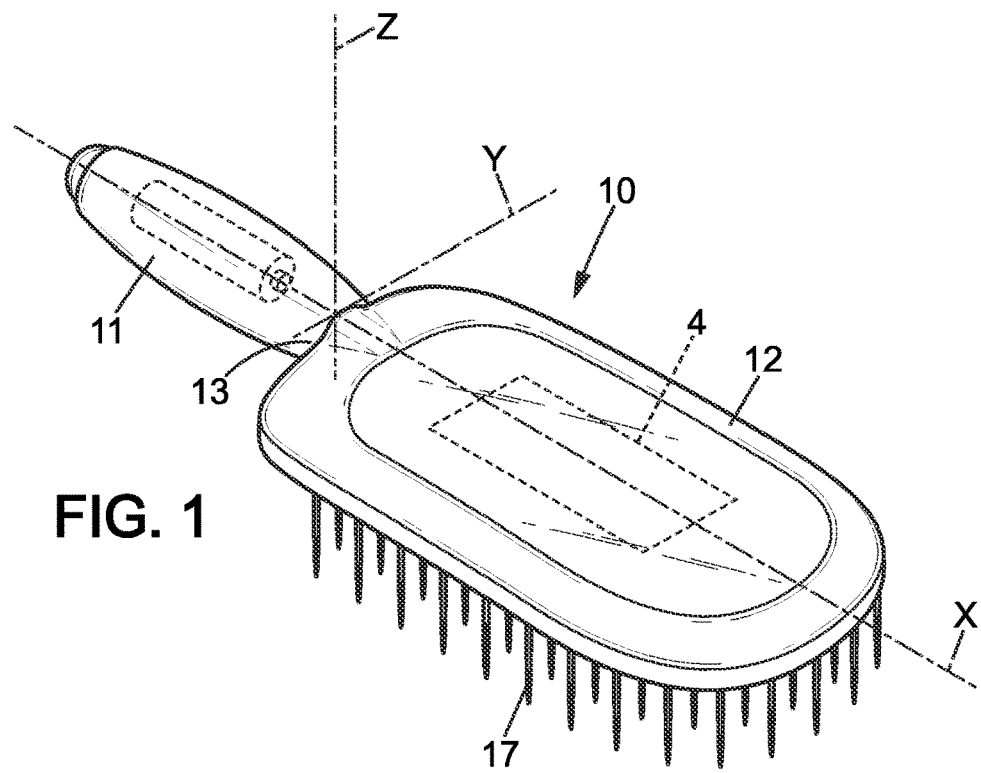
FIG. 1 is a general perspective view of a hairstyling tool according to the invention.

FIG. 1 represents an example of a hairstyling tool of the invention, in this case a hairbrush 10. The hairstyling tool could also be a comb or another similar type of implement.

The hairbrush comprises a handle 11 (also called a 'grip') and a body 12 which is provided with teeth 17 and/or bristles on its front face 14, which can engage with hair of a user. When said brush is moved through the hair, a styling (or combing) action takes place.

As illustrated in FIG. 1, the handle 11 and the body 12 succeed one another in a longitudinal direction X. The handle in the example illustrated is substantially a cylinder with X as its axis of revolution and is connected to the body 12 by a transition region 13, which may be of reduced cross-section compared to the main cross-section of the handle. The body 12 mainly lies in a plane in the longitudinal direction X and a transverse direction Y, while the teeth extend in a third direction Z referred to as the radial direction.

Figure 2:
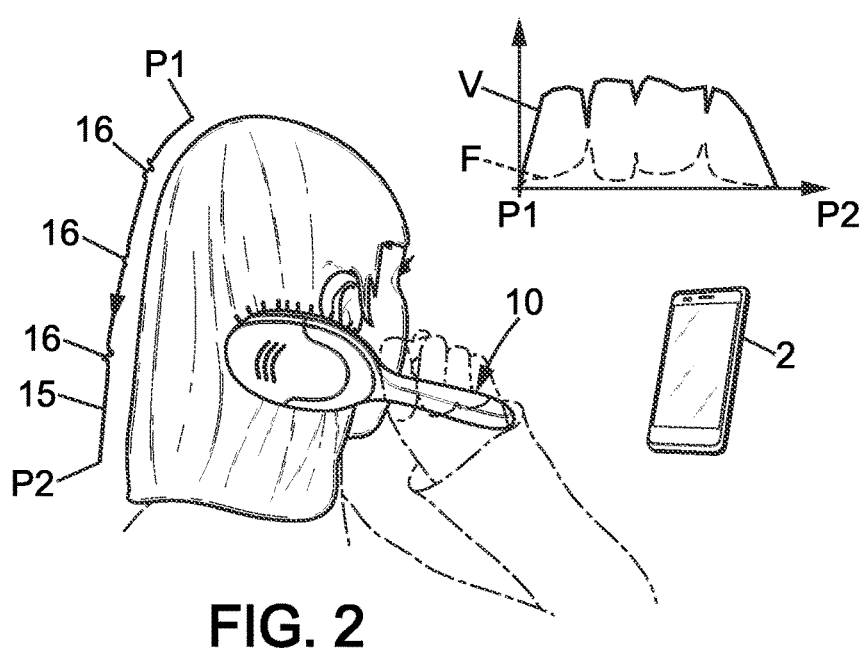
FIG. 2 is a general perspective view of the hairstyling tool of FIG. 1 while being used by a user.
Figure 3:
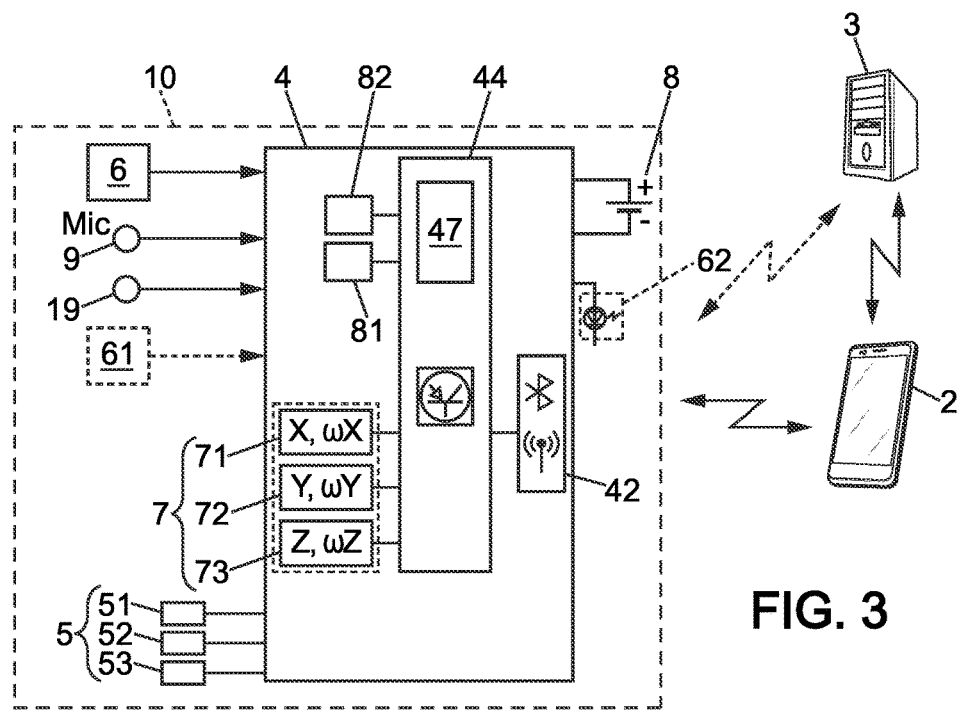
FIG. 3 shows a schematic diagram of the hairstyling tool of FIG. 1 in an informational system of which it is a part.
Figure 4:
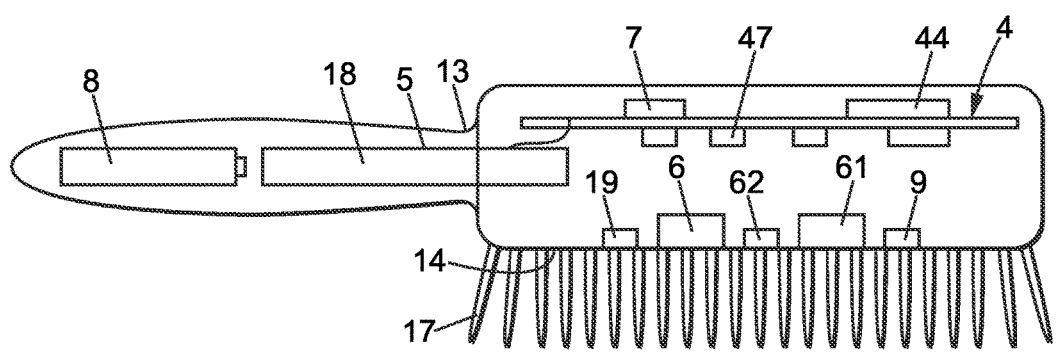
FIG. 4 shows a schematic longitudinal sectional view of the hairstyling tool of FIG. 1.

Referring to FIGS. 2 to 4, the brush further comprises a battery 8 for storing electrical energy. The battery is intended to supply power to all electrical and electronic equipment housed in the brush, which will be detailed below. This battery may be of the rechargeable type and recharged through an external connection or without connection by means of an alternating magnetic flux (wireless charging stand). A luminous flux charging solution is not excluded, for example by means of an arrangement of photodiodes, arranged on the surface of the body.

The brush further comprises an electronic control unit 4 extending inside the body substantially within the XY plane, whose composition and functions will be detailed below.

The brush comprises at least one movement sensor or accelerometer 7. In the example illustrated, it is a six-axis sensor capable of measuring linear accelerations in the three orthogonal directions X, Y and Z as well as rotational movements about the three orthogonal directions X, Y and Z. For the detection of rotational movements, it uses miniature gyroscopes 71,72,73, preferably integrated into a single electronic package (also comprising the linear accelerometers, for example in a MEMS circuit) installed directly on the board of the control unit.

Using the raw data gathered by the accelerometers and gyros, it is possible to perform integration calculations to determine the movements of the brush.

It should be noted, however, that the acceleration caused by gravity g must be removed, which can be done by software filtering operations or by the use of a supplemental multi-axis tilt sensor.

The movement sensor could be much simpler however, for example having two axes.

The brush comprises at least one wireless communication means 42, for example a Bluetooth™ or WiFi interface, arranged on the board of the control unit. This interface allows data transmission from the brush to a remote entity; the brush may also receive data via this interface.

In the example shown, the remote entity is a mobile device known as a smartphone 2. However, the remote entity could be a computer directly connected to the Internet or a data server.

Advantageously according to the invention, the brush may also comprise at least one force sensor 5, which in the example illustrated is represented as an instrumented rod 18, arranged at least in the transition region 13 mentioned above. Said rod 18 absorbs the stresses between the handle and body.

In the example illustrated, the force sensor may be a strain gauge and is adapted to measure three components 51,52,53, i.e. a torsion about axis X, a bending about axis Y, and a bending about axis Z. Said force sensor therefore measures the main forces exerted between the handle 11 held by the user and the body 12 engaged with the hair of said user, during the hairstyling movement.

As represented in FIG. 2, a hairstyling movement begins at a starting point P1, and then follows a generally curved line 15 to an end point P2. The speed V of motion and the forces F evolve during this movement, as exemplified in the graph; in particular, during the movements, there may be more resistant spots or areas 16. The accelerometers and force sensor allow determining the speed and regularity of the styling gesture, the rotation of the brush during the styling gesture, the length of the curve followed by the styling gesture, and the time taken to travel said curve.

Advantageously, the brush may further comprise at least one camera 6 and/or optical sensor 61, arranged on the front face 14 of the brush body; their lens is therefore directed outwardly in order to gather optical information concerning the hair and/or scalp.

One or more lights 62 (or LEDs), operating within the visible range or the infrared range, are also arranged on the front face 14, which allows illuminating the work area during the hairstyling movement.

The optical sensor 61 can have a definition level that is more or less high, from several hundred pixels to millions of pixels; the same is true for images captured by the camera 6.

It is understood that the images may be captured under different lighting conditions created by the lights 62, such that it may be possible to perform optical radiography of the hair and/or scalp, in particular in order to obtain information about their health.

Advantageously, one (or multiple) optical sensor(s) may be provided that are dedicated to optical analysis of the hair, and at least one other optical sensor dedicated to optical analysis of the scalp.

It should be noted that the images of the scalp may be displayed on the smartphone screen, so that the user can see firsthand the condition of his or her hair and scalp at high magnification, which is normally inaccessible. This function can be called the "scalp/hair webcam function".

The hairbrush may further comprise a microphone 9, arranged for example on or near the front face 14. This microphone is suitable for measuring the friction and vibration generated by hairstyling movements. The control unit 4 is configured to format and transmit data corresponding to the friction and vibrations picked up by the microphone.

In addition, the hairbrush may further comprise an electric field sensor 19, also arranged on or near the front face 14 and suitable for measuring an electric field E generated by the electrostatic charges resulting from hairstyling movements. The control unit 4 is configured to format and transmit data corresponding to the electric field measured during the hairstyling movement.

In addition, the hairbrush may further comprise a temperature sensor 81 and/or humidity sensor 82, for capturing characteristics of the atmospheric environment that may influence the hairstyling operations and therefore affect analysis of the forces and images collected during the hairstyling movements.

The control unit 4 comprises a microcontroller 44 responsible for managing the input/output interfaces for the sensors, lights, and communication interface, the main functions in active mode, and the wake and sleep functions which will described below. The control unit 4 is configured to be able to store in memory 47 the raw or processed data collected during the hairstyling movement or movements, prior to subsequent transmission to the remote entity 2.

The data collected during the hairstyling operations can be transmitted, with or without preprocessing, by the smartphone 2 to a server 3 which comprises one or more applications responsible for analyzing the data concerned, in order to formulate recommendations for hair care or products to be applied to the hair in question.

The recommendations for hair care or for the application of products sent by the server can take various forms, for example messages intended for display on the smartphone.

It should be noted that sending data through the smartphone is not required, as the data can be transmitted directly from the brush to the server over a wireless link.

It should also be noted that it is possible to manage multiple different users for a given hairbrush. In addition, each hairstyling tool of the invention is identified as a unit to allow it to be unambiguously recognized by the smartphone and/or remote server.

The battery may be of a conventional type and housed in the handle as shown; however, the battery may be in any form and be housed elsewhere in the brush or comb. Similarly, the control unit could be arranged differently and is not necessarily housed in the body, particularly for a comb.

The electronic unit may manage a clock indicating the date and time, so that the hairstyling operations can be time-stamped. The brush may receive messages setting the clock date and time, via the communication interface from the server.

The linear accelerometers are used for waking the control unit when substantial movements are captured by these accelerometers, and for putting the control unit to sleep after a predetermined time has passed with no substantial movement captured by the accelerometers; this ensures the lowest possible power consumption, especially during periods when the brush is not in use.

A predetermined acceleration threshold may be defined, above which the control unit wakes up and below which the control unit remains asleep, to prevent the control unit from waking when the brush has been set down in a moving vehicle such as a car, train, boat, or plane. A jolt generated by user manipulation does wake the control unit 4, however.

For the analysis of data collected during the hairstyling movement, particularly displacements, movements, stresses, optical information, the electric field, etc., a first analysis step may be performed by the microcontroller 44 of the control unit 4 to enable transmitting less data to the remote unit. However, it remains possible for the control unit 4 to transmit some or all of the data in raw form. If the collected data passes through a smartphone type of mobile device 2, this device may perform a second step of data analysis, in order to display some of this data to the user on the display screen (scalp/hair webcam function) and to be able to transmit higher-level data to the server 3 mentioned above.

The server 3 may perform a third step of data analysis, in particular comparing the received data with reference data stored in a database concerning hair, the scalp, and any other relevant information. This allows remote analysis based on an established hair/scalp database and on knowledge of prior data concerning the user in question.

More specifically, advantageously according to the invention, the server 3 acts as a centralized platform for collecting a large amount of information about hairstyling operations by a multitude of users.

Furthermore, this centralized platform can collect and store data gathered for a specifically identified brush or even identified user, over a significant period or even over a long period. The centralized platform can thus analyze changes over a long period, particularly changes concerning the forces and hairstyling movements of a particular user, which allows customizing the care recommendations message provided to that user, based on data specific to that user.

Note that the platform can do its analysis by learning a large amount of data received from users of connected hairstyling tools.

It should also be noted that as an alternative, the role of the centralized platform could be filled by the smartphone 2.

In all cases, the remote entity, preferably the centralized platform hosted on the server 3, can send recommendations back to the user as indicated above, based on the data analysis, for example in the form of an SMS message, email, or other form.

The invention claimed is:

1. A system comprising a hairstyling tool and a remote entity configured to be connected together by a wireless connection, the hairstyling tool being a comb or a hairbrush,
    the hairstyling tool comprising:
        a handle and a body, provided with teeth and/or bristles,
        at least one movement sensor,
        at least one three sensor configured to measure a torsional or bending stress exerted between the handle held by a user and the body engaged with the hair of said user,
        at least one electric field sensor suitable for measuring an electric field generated by the electrostatic charges resulting from hairstyling movements,
        an electronic control unit, configured to capture and format signals provided by the at least one force sensor, and by the at least one movement sensor, and the at least one electric field sensor,
        at least one wireless communication coupler suitable for data transmission to the remote entity,
        wherein the wireless communication coupler is configured to transmit to the remote entity data corresponding to information on the movements executed by the hairstyling tool through the hair and stresses entailed therefrom, as well as electric field sensed along said executed movements,
        wherein the remote entity comprises at least one application configured to analyze the received data to formulate recommendations for hair care or products to be applied to the hair of the user, wherein the remote entity is configured to provide the recommendations to the user of the hairstyling tool via a display screen.

2. The system according to claim 1, wherein the hairstyling tool further comprises at least one camera and/or optical sensor suitable for capturing images of the hair and/or scalp, the electronic unit being configured to format and transmit these images.

3. The system according to claim 1, wherein the hairstyling, tool further comprises at least one memory space suitable for storing data collected during the hairstyling movement or movements, prior to subsequent transmission to the remote entity.

4. The system according to claim 1, wherein the remote entity is formed of a mobile device, configured to display some of the data transmitted by the hairstyling tool and provide information to the user about the hair being styled.

5. The system according to claim 1, wherein the remote entity comprises both a mobile device and a computer server that can connect to the mobile device in order to exchange summary data concerning the hairstyling.

6. The system according to claim 1, wherein the hairstyling tool further comprises at least one microphone suitable for measuring the vibrations generated by the hairstyling movement, the electronic unit being configured to format and transmit the corresponding data.

* * * * *